United States Patent
Lee

(10) Patent No.: US 6,331,112 B1
(45) Date of Patent: Dec. 18, 2001

(54) ENDODONTIC PROBE SYSTEM

(76) Inventor: Charles Q. Lee, 8343 Acuff La., Lenexa, KS (US) 66215

( * ) Notice: Subject to any disclaimer, the term of this patent is extended or adjusted under 35 U.S.C. 154(b) by 0 days.

(21) Appl. No.: 09/738,820

(22) Filed: Dec. 15, 2000

(51) Int. Cl.$^7$ .................................................. A61C 5/02
(52) U.S. Cl. ........................................ 433/102; 433/224
(58) Field of Search ............................ 433/224, 102, 433/72

(56) References Cited

U.S. PATENT DOCUMENTS

| | | | |
|---|---|---|---|
| 3,318,000 | * 5/1967 | Paris | 433/224 |
| 4,332,561 | 6/1982 | McSpadden | 433/102 |
| 4,447,206 | 5/1984 | Ushiyama | 433/27 |
| 4,850,867 | 7/1989 | Senia et al. | 433/102 |
| 5,423,677 | 6/1995 | Brattessani | 433/72 |
| 5,915,964 | * 6/1999 | Walia | 433/102 |
| 6,024,565 | 2/2000 | Sicurelli et al. | 433/102 |
| 6,053,735 | 4/2000 | Buchanan | 433/224 |

OTHER PUBLICATIONS

Morphis et al.; Study of the Apices of Human Permanent Teeth with the use of a Scanning Electron Microscope; in Oral Surgery Journal Feb. '94.

Berutti; Measurement of the Apical Foramen: in Dentistry Today Sep. 98.

Gani et al.; Apical Canal Diameter in the First Upper Molar at Various Ages; in Journal of Endodontics Oct. 99

Miyashita et al; Root Canal System of the Mandibular Incisor; in Journal of Endodontics Aug. 97.

Cohen et al; Pathways of the Pulp, 1994 p. 201.

Ingle, et al. ; Endodontics, 1994; pp 192–3.

Weine; Endodontic Therapy 1996; p 402.

* cited by examiner

Primary Examiner—Cary E. O'Connor
(74) Attorney, Agent, or Firm—Wm. Bruce Day

(57) ABSTRACT

An endodontic probe system comprises a measuring kit of a plurality of flexible rods for insertion as probes into a root canal for determining the apical aperture diameter. Each rod has a tip end with a diametrally enlarged end ball structure so that a user obtains a precise tactile sensation when passing the end ball through the apical aperture. A variety of different end ball shapes are disclosed. Measurement of the apical aperture diameter is important to determine so that the root canal may be properly and entirely cleaned without unnecessary reaming or enlarging the diameter of the apical aperture.

8 Claims, 2 Drawing Sheets

ENDODONTIC PROBE SYSTEM

FIELD OF THE INVENTION

The present invention relates to endodontic probes and in particular to endodontic measuring probes used for determining the diameter of the tooth apical aperture and the length of the root canal so that the root canal may be properly cleaned prior to filling.

BACKGROUND OF THE INVENTION

Precise determination of tooth root canal length and the diameter of the apical aperture is vitally important for correct endodontic cleaning and filling. The root canal must be precisely reamed and the pulp tissue completely removed because leaving some of the pulp tissue may lead to abscess. Removing more of the root canal structure than necessary is not desired and leaving pulp tissue within the canal is to be avoided. The dentist must know precisely the location and diameter of the apical aperture of the root canal in order to render the most effective and painless treatment.

The difficulty with completely cleaning the root canal is that the canal tapers to a narrow neck at the root apex and then widens again as it approaches the site of exiting from the root. This has been described as a funnel shape or even as the shape of a morning glory flower. The dentist must be aware of the probable canal configuration present and any common variants that might be present, the estimated length of the root(s), the site of exiting of the canal(s), and the estimated width of the canal(s). This is done by analyzing the preoperative radiographs available.

It has been clinically established that the root canal must be cleaned as thoroughly as possible to remove any remaining pulpal tissues, bacteria, toxins and debris. If the cleaning instruments or irrigating solutions are thrust through the apical foramen, tissues surrounding the tooth root may become inflamed or infected, leading to intense pain which may require surgery. Therefore, it is critical that the dentist know precisely the location and diameter of the apical foramen.

OBJECTS OF THE INVENTION

It is an object of the present invention to provide an endodontic measuring kit which accurately measures the length and the diameter of the apical aperture of the tooth canal; it is a further object of the invention to provide such a measuring kit or system which does not require repeated x-rays for the dentist to determine the length of the root canal and diameter of the apical aperture; to provide a set of measuring instruments with graded tip diameters for observing tooth depth; to provide a set of measuring instruments having tip ends specially designed for tactile sensitivity so that the dentist can precisely determine the location and diameter of the apical aperture. It is a further object of the invention to enable a dentist to provide an apical plug of proper size and shape.

Other objects and advantages of the present invention will become apparent from the following description and drawings.

DESCRIPTION OF THE PREFERRED AND ALTERNATE EMBODIMENTS

Figure 1:
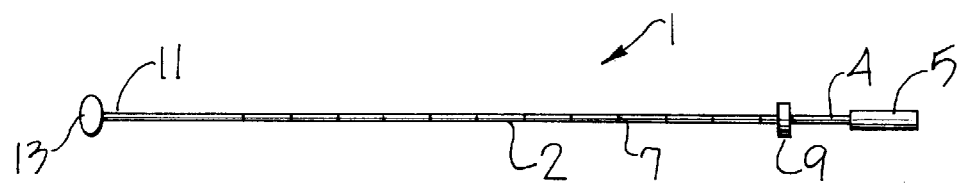
FIG. 1 is a plan view of an endodontic measuring rod comprising the present invention.

Referring more specifically to the drawings, which are provided herewith for illustrative purposes and not to be intended as limiting, the present invention comprises a kit created about an endodontic measuring rod 1, FIG. 1, and generally consists of a shank 2 terminating at a handle end 4 in a handle 5. The handle 5 can be configured for hand use by a dentist or it can be configured for insertion into the chuck of a machine tool. The shank 2 includes a scale 7 of selected units to determine the length of the endodontic canal. Sleeved on the shank 2 is a slidable stop 9, such as of elastomeric material, so that it grips the shank 2 and can be slid along the length of the shank to mark the length of the endodontic canal. At the tip end 11 of the shank 2 is a diametrally enlarged end ball structure 13. The end ball structure 13 is of larger diameter than the shank 2 and provides a tactile sensation when passing through the apical aperture. The shank is made of standard surgical stainless steel, nickel titanium or any suitable material.

Figure 2:
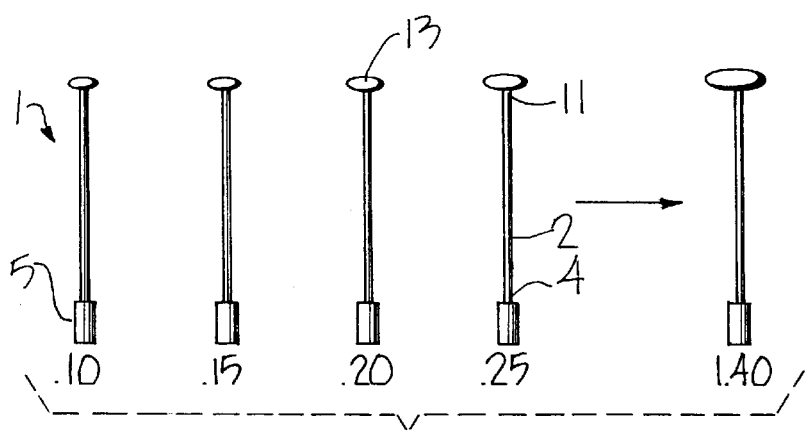
FIG. 2 is a plan elevational view of a series of measuring rods such as shown in FIG. 1 which are of progressive sizes.

Referring to FIG. 2, an array of different sizes of endodontic measuring rods 1 are provided to comprise an endodontic measuring kit. The end ball structures in the endodontic measuring kit may range in size from 0.1 millimeters to 1.40 millimeters, as is common in presently available endodontic measuring kits which use rods only and in which the rods do not have the diametrally enlarged end ball structures of the present invention.

Figure 3:
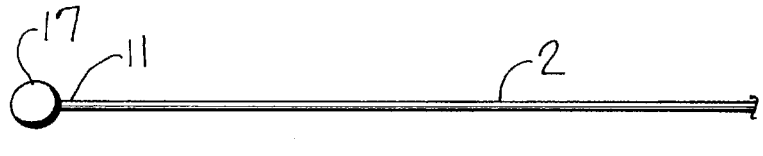
FIG. 3 is a plan view of an endodontic measuring rod showing one form of the rod tip, the end of which is believed to be the desired or best embodiment configuration.
Figure 4:
FIG. 4 is a plan view of an endodontic measuring rod showing another form of rod tip.
Figure 5:
FIG. 5 is a plan view of an endodontic measuring rod showing another form of measuring tip.

A series of endodontic measuring rods 1 are shown in connection with FIGS. 3 through 9. For purposes of illustration, none of the shanks 2 in FIGS. 3 through 9 include handles 5 nor is the scale 7 or slidable stop 9 shown thereon. All have end ball structures 13 but an end ball structure of different configuration is disclosed in connection with each of the FIGS. 3 through 9. In FIG. 3, a round ball 17 is shown. The FIG. 3 embodiment is believed to be the preferred embodiment and is believed to be the best mode of practicing the invention. FIG. 4 shows an oval ball end structure 19 in which the longitudinal axis of the oval ball 19 is coaxial with the longitudinal axis of the shank 2. FIG. 5 discloses an oval ball 21 in which the long axis of the oval ball is normal or 90 degrees (90°) from the long axis of the shank 2.

Figure 6:
FIG. 6 is a plan view of an endodontic measuring rod showing another form of rod tip.
Figure 7:
FIG. 7 is a plan view of an endodontic measuring rod showing yet another form of measuring rod tip.
Figure 8:
FIG. 8 is a plan view of endodontic measuring rod showing another form of rod tip.
Figure 9:
FIG. 9 is a plan view of endodontic measuring rod showing yet another form of rod tip.

FIG. 6 shows a teardrop shape ball 23 in which the apex of the teardrop points into the shank 2. FIG. 7 shows the opposite orientation 24 of the teardrop shaped ball in which the apex of the ball points away from the shank 2. FIG. 8 discloses a round ball 26 with a spike tip 27 therebelow. FIG.

9 discloses a double ball tip 28 in which two balls of equal diameter are slightly spaced from each other along the shank 2.

Each of these end ball structure shapes may provide a slightly different tactile sensation and while the inventor prefers the roundball 17 or sometimes the transverse oval ball 21, additional experimentation and clinical trials may be needed before determining which is the overall best shape. The end ball structure 13 may be coated or solid, or of a different type of material than the shank 2 so that it has a higher radiological density than the shank 2 to enable the end ball structure to show better-on x-ray photographs than the shank, if x-rays are used. The end ball 13 may be of the same material, yet still be noticeable on a radiograph, because of its higher density.

Figure 10:
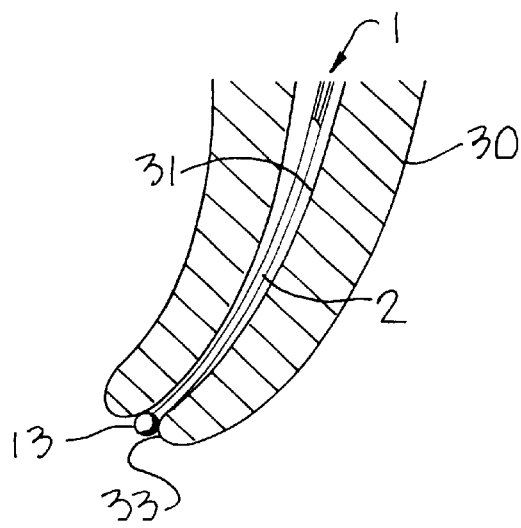
FIG. 10 is a fragmentary elevational view of the endodontic measuring rod inserted into a root canal.
Figure 11:
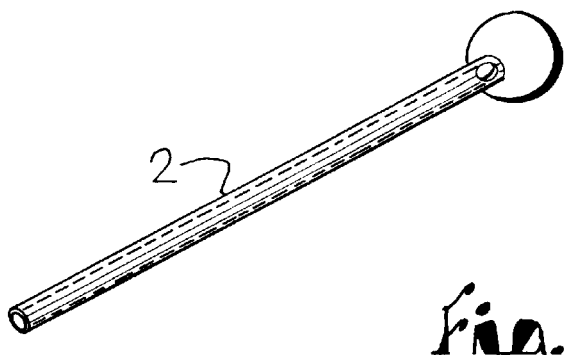
FIG. 11 shows an alternative version with an interior irrigation tube.

FIG. 10 shows a tooth root 30 with a root canal 31 terminating in an apical aperture 33. The location and depth of the apical aperture 33, and the length of the root canal 31, must be precisely determined. As shown in FIG. 11, the endodontic measuring rod 1 is shown inserted into the root canal 31 with the shank 2 extending the length thereof and the end ball structure 13 locating the apical aperture 33. The tactile sensation sensed by the dentist is slight and comprises a slight resistance as the end ball structure passes through the aperture 33 followed by a cessation of resistance. This slight "bump" when encountering the apical aperture 33 is tactilely more precise than the prior art use of rods of different diameters, as with the use of a rod only it is more difficult to determine the precise location of a constriction, such as the apical aperture 33. The shank 2, FIG. 10, can be a hollow tube to use as an irrigation device. The end ball 13 is to block any irrigation solution beyond the apex.

FIG. 11 shows a shank 2 with a hollow interior passage and an outlet at the ball adjoining the ball end for irrigation of the root canal. A syringe can be connected to the shank and used to inject a water solution.

After determination of the length of the root canal 31 and the size or diameter of the apical aperture 33, an apical plug can be inserted. These plugs can be made of calcium hydroxide, hydroxyapatite or nickel titanium material or other biocompatible materials. Because the dentist has determined the size and shape of the apical aperture, a plug of precise size and shape to match the aperture can be selected and inserted into the aperture 33. The apical plug can be connected to a carrier rod then separated after placement, or can be connected to a gutta percha tip or bonded to the gutta percha tip then separated.

The invention disclosed herein is not to be interpreted as limiting, except insofar as set forth in the following claims.

What is claimed and desired to be secured by letters patent is:

1. An endodontic measuring kit comprising:

a plurality of flexible rods for insertion as probes into an endodontic canal for determining the apical aperture diameter;

said rods having tip ends with diametrally enlarged end ball structures so that a user obtains a precise tactile sensation when passing the end ball structure through the apical aperture.

2. The endodontic measuring kit set forth in claim 1 wherein said end ball structures range in size from 0.10 millimeter to 1.40 millimeter.

3. The endodontic measuring kit set forth in claim 1 wherein said end ball structure is a flattened oval having its long axis normal to the longitudinal axis of the rod.

4. An endodontic measuring probe comprising a generally straight, flexible rod for insertion into an endodontic canal for determining the apical aperture diameter, said rod including a shaft with measurement indicia and having a tip end with an enlarged ball structure so that a user obtains a precise tactile sensation when passing the end ball through the apical aperture.

5. An endodontic measuring kit comprising a plurality of flexible rods for insertion as probes into an endodontic canal for determining the apical aperture diameter, said rods having tip ends with diametrally enlarged end ball structures generally ranging in size from 0.10 millimeter through 1.40 millimeter for selection by a user and so that said user obtains a precise tactile sensation when passing the end ball structure through the apical aperture.

6. The endodontic measuring kit set forth in claim 5 wherein the rods are of a smaller diameter than the tip end ball structures.

7. The endodontic measuring kit set forth in claim 5 including plugs of a selected size and shape corresponding to said end ball structures, said plugs being insertable into the endodontic canal to seal the apical aperture.

8. The endodontic measuring kit set forth in claim 5 wherein the rods are hollow with longitudinal passages to provide irrigation for the root canal.

\* \* \* \* \*